United States Patent [19]

Binker et al.

[11] Patent Number: 4,692,162
[45] Date of Patent: Sep. 8, 1987

[54] SANITARY NAPKIN WITH INTEGRAL DISPOSAL WRAPPER

[76] Inventors: Norman Binker; Sandra Miranda, both of 4344 Winchester, Apt. #15, Los Angeles, Calif. 90032

[21] Appl. No.: 853,174

[22] Filed: Apr. 17, 1986

[51] Int. Cl.$^4$ .............................................. A61F 13/16
[52] U.S. Cl. ................................................ 604/385 R
[58] Field of Search ..................... 604/385.1, 358, 386, 604/387

[56] References Cited

U.S. PATENT DOCUMENTS

| | | | |
|---|---|---|---|
| 3,230,956 | 1/1966 | Kargul | 604/385.1 |
| 3,274,999 | 9/1966 | Robinson | 604/385.1 |
| 3,604,423 | 9/1971 | Fraser | 604/385.1 |
| 3,973,567 | 8/1976 | Srinivasan et al. | 604/385.1 |
| 4,182,336 | 1/1980 | Black | 604/385.1 |
| 4,581,027 | 4/1986 | Alvarado | 604/385.1 |

Primary Examiner—John D. Yasko
Attorney, Agent, or Firm—Bruce A. Jagger; Natan Epstein

[57] ABSTRACT

A disposable sanitary napkin comprising an elongated absorbent pad having two opposite faces extending between two pad ends and two side edges has a reversible bag of substantially impermeable material affixed to one pad face such that the bag may be reversed to wrap and contain the pad after the used pad has been rolled up for hygienic disposal after use.

5 Claims, 6 Drawing Figures

U.S. Patent  Sep. 8, 1987  4,692,162
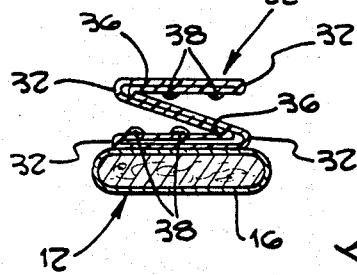
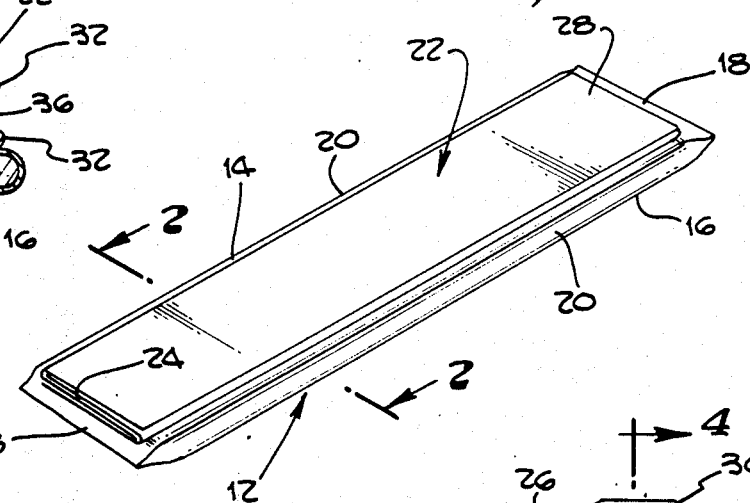
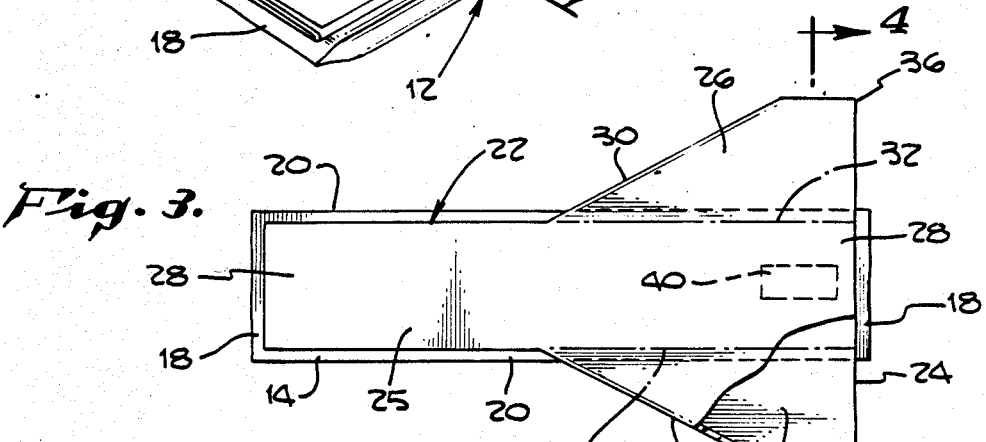
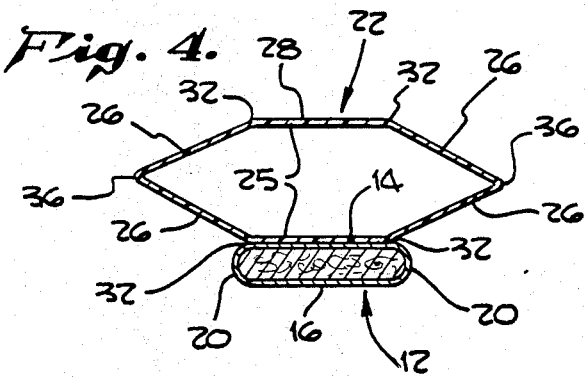
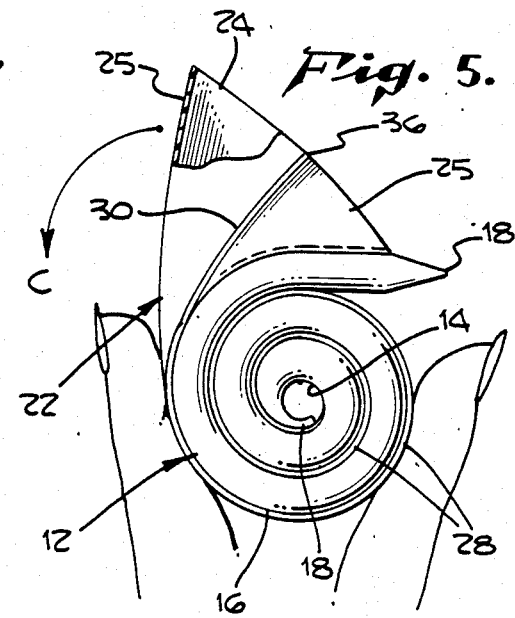
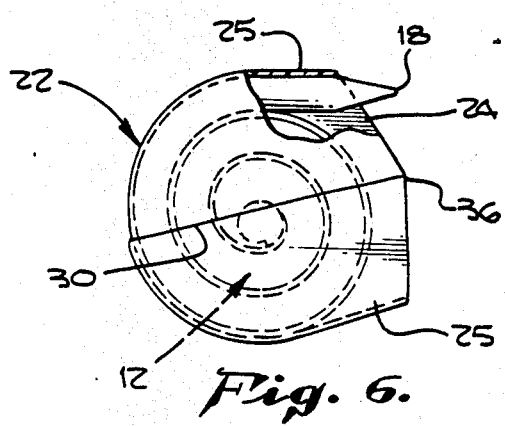

SANITARY NAPKIN WITH INTEGRAL DISPOSAL WRAPPER

FIELD OF THE INVENTION

The present invention is directed generally to the field of articles pertaining to feminine hygiene and is more particularly directed to an improved sanitary napkin comprising an integral disposal bag attached thereto for more sanitary and aesthetic disposal.

BACKGROUND OF THE INVENTION

Sanitary napkins of the type comprising an elongated absorbent pad have long been in widespread use. In the most commonly used type, the pad is of relatively simple construction, consisting of a permeable envelope filled with absorbent material such as cotton or the like, and having a generally planar rectangular configuration with two long sides extending between two opposite pad ends and two opposite main absorbent faces. Normally the pad is used on only one side, and when the one face becomes soiled, the pad is discarded.

While efforts have been made in the past to provide integral wrappers for more hygienically disposing of the use pad, no completely satisfactory solution is known to this applicant and a continuing need for an improved sanitary napkin with integral disposal wrapper continues to exist.

SUMMARY OF THE INVENTION

The present invention improves over the prior art by providing a sanitary napkin comprising an elongated absorbent pad having two opposite faces extending between two pad ends and two side edges. The improvement comprises the provision of a reversible disposal bag affixed to one of the pad faces, the opposite pad face remaining clear and uncovered for use in the conventional manner. After use, the pad is rolled up on the side of the soiled pad face, the disposal bag being affixed to the exposed or outer face of the rolled pad. The bag is then reversed, i.e., turned inside out, over the rolled pad so as to cover and envelop the soiled, rolled-up pad. The disposal procedure is generally similar to the common expedient of rolling up a pair of socks and turning over the open end of one of the socks to envelop and contain the rolled pair.

The reversible bag is desirably made of a substantially impermeable material such as thin plastic sheet material. Before and during use the disposal bag is folded flat against the pad and does not substantially affect the manner of usage of the pad except in so far as it limits the use of the pad to a particular pad face since the other pad face is substantially covered by the folded impermeable bag. In practice, this is not a limitation of any importance since such pads are typically used on one side only. The disposal bag does not substantially add to the weight or bulk of the sanitary napkin nor affect the comfort of its use.

The disposal bag may be conveniently made by joining two particularly shaped sheets along all edges except one, the unsealed edge forming the open end of the bag. The resulting bag in an unfolded condition has a closed narrow end and a wide, reversible, open end as will be described below. The outer surface of one of the sheets comprising the bag is secured to one face of the absorbent pad as by a suitable non-toxic adhesive. In its folded configuration, the bag is an elongated rectangular strip lying flat against one face of the absorbent pad. The folded bag is readily flexible and does not materially increase the overall thickness of the pad.

For disposal, the used pad is preferably rolled up, beginning at the closed end of the bag and proceeding towards the open bag end, with the soiled face of the pad oriented towards the center of the roll and the bag side facing outwardly. The pad is then maintained in the rolled condition in one hand while with the other hand the user unfolds and opens the wide end of the bag, and then reverses the open end over the rolled pad. The reversed portion of the bag is dimensioned to snuggly envelop the rolled pad as a wrapper so as to retain the pad in a compact rolled package of relatively sanitary appearance. The disposal operation is accomplished quickly and without fumbling for separate wrappers.

The addition of the attached disposal bag requires no modification to currently used absorbent pad structures or the materials used in the same, and provides a low cost solution to an ongoing disposal problem.

BRIEF DESCRIPTION OF THE DRAWINGS

FIG. 1 is a perspective view of the improved sanitary napkin showing the disposal bag attached thereto in its normal folded state before or during use.

FIG. 2 is a section taken along line 2—2 in FIG. 1 showing the bag in a partially folded condition.

FIG. 3 is plan view of the sanitary napkin of FIG. 1 showing the disposal bag in an unfolded condition.

FIG. 4 is a cross-section of the unfolded bag and attached pad taken along line 4—4 in FIG. 3.

FIG. 5 shows the sanitary napkin rolled up and the reversible bag being opened just prior to reversal over the rolled pad.

FIG. 6 shows the sanitary napkin wrapped by the reversed disposal bag and ready for discarding.

DETAILED DESCRIPTION OF THE PREFERRED EMBODIMENTS

With reference to the drawings, FIG. 1 shows an absorbent menstrual pad 12 having an upper face 14 and an opposite lower face 16 visible in FIG. 4, but not in FIG. 1, two opposite pad ends 18 and two pad edges 20. The pad 12 may consist of a permeable envelope, typically of paper, enclosing an absorbent filling such as cotton or the like, as best seen in the FIG. 4 cross section. A disposal bag 22 is attached to the pad face 14 by means of a non-toxic surgical adhesive. The construction of the disposal bag 22 will be best understood by reference to FIGS. 2, 3 and 4. The bag 22 consists of two superimposed planar sheets 25 of equal size and having an initial, unfolded shape as shown in FIG. 3. Each sheet 25 has a relatively narrow, elongated rectangular portion 28 connected to the narrow end of a flaring generally trapezoidal portion 26. The bag 22 is made by joining the two sheets continuously along all edges, except the long base of the trapezoidal portion 26, so as to leave an open bag end 24. The wide end of the bag is folded as shown in FIGS. 2 and 3. The two generally triangular flaring side portions along the divergent sides 30 of the joined, superimposed sheets are folded inwardly along fold lines 32 to a state where the divergent edges 30 are brought from the initial condition of FIG. 4 to the partially folded condition of FIG. 2, wherein the flaring side portions are tucked in and lie between the central portions of the joined overlying sheets 25. The corners 36 of the wide end of bag 22 are displaced from their outlying positions of FIGS. 3 and 4 inner positions shown in FIG. 2. The folding of the bag 22 is completed by flattening the same against the pad 12 to a final condition as shown in FIG. 1. The folds are made so that in the folded condition of FIG. 1 the bag 22 is a rectangular elongated strip somewhat undersized in relation to the pad face 14 and of uniform width between the closed end 28 and the open end 24. One side of the folded bag 22 is affixed to face 14 of the absorbent pad 12 substantially along the entire length of the bag between the two ends 24, 28 by means of a suitable non-toxic adhesive such as a surgical adhesive to securely retain in place under the absorbent pad 12 while the pad is worn.

After use, the pad 12 is rolled up into a spiral as shown in FIG. 5 over the soiled pad face 16 beginning from the closed bag end 28 and with the bag side 14 of the pad facing outwardly of the roll. The pad 12 is held in this rolled condition with one hand while the wide end 24 of the bag 22 is unfolded and opened by separating the two sheets 25 along the edge 24. The open end of the bag is then pulled over the rolled pad 12 as indicated by arrow c in FIG. 5 to the reversed condition shown in FIG. 6 with the rolled pad tucked into the reversed bag 22. The wide trapezoidal portion 26 of the bag 22 is reversed and turned inside out over the rolled absorbent pad 12 which is then substantially contained and wrapped within the reversed portion of bag 22, as in FIG. 6. The wide portion 26 of the bag is also reversed over the narrow bag portion adjacent the closed bag end 28 which remains affixed flat against the rolled pad surface 14 and secured between adjacent layers of the spiral formed by the rolled pad to better retain the bag to the pad, so that the entire package may be discarded without possibility of the rolled pad 12 becoming disengaged and falling out of the bag 22. The bag reversal is accomplished quickly and easily to produce a package which can be handled more conveniently and hygienically than has been possible until now. The bag 22 may be made of thin plastic sheeting such as polyethylene sheet material which is impermeable to allow sanitary handling of the soiled pad during disposal. A strip 40 of single-sided adhesive tape may also be provided on the inside surface of the bag as shown in FIG. 3 for use in taping closed the open end of the bag after its reversal over a used, rolled-up pad 12 for hygienic disposal. The adhesive strip is peeled off by the user from the position shown in the drawing and placed over the joined edges of the open bag end to keep the bag closed.

Although a particular embodiment of the invention has been shown and illustrated for purposes of clarity and by way of example only, many changes, substitutions and modifications to the described embodiment will become apparent to those possessed of ordinary skill in the art without departing from the spirit and scope of the invention, which is defined only by the following claims.

What is claimed is:

1. A disposable sanitary napkin comprising an elongated absorbent pad having two opposite faces extending between two pad ends and two side edges;
   a reversible bag affixed to one said face of said absorbent pad between said pad ends;
   said bag including a wide portion including an open bag end oriented towards one of said pad ends and an elongated narrow bag portion terminating in a closed bag end oriented towards the opposite pad end, said folded bag being affixed to said pad face at both bag ends, said wide portion being normally folded to a width comparable to said narrow portion and flat against said pad face prior to and during use of said pad, said wide portion being reversible over the rolled pad as a disposal wrapper such that the bag may be reversed to receive and contain said pad for hygienic disposal after use and after said pad has been rolled up over the other of said pad faces with the bag bearing pad face facing outwardly of the roll, the rolling beginning with the pad end proximal to the closed end of the bag, said narrow portion being disposed and held between coil turns of the roll so as to at least partially roll up with said pad so as to more securely anchor said bag to said pad during reversal of said wide portion.

2. The sanitary napkin of claim 1 wherein said wide end is normally folded to a flat elongated rectangular shape of uniform width with said narrow portion.

3. The sanitary napkin of claim 1 wherein said reversible bag is made of two superimposed sheets each having a wide generally trapezoidal portion and a narrow elongated rectangular portion extending from the short base of said trapezoidal portion, said two sheets being joined along all edges except the long base of said trapezoidal portion to form an open bag end.

4. The napkin of claim 3 wherein said wide bag portion is folded by in-turning flaring portions of said trapezoidal bag portion.

5. The napkin of claim 3 wherein said bag is made of thin plastic sheeting.

* * * * *